United States Patent [19]

Thurman

[11] Patent Number: 4,775,482
[45] Date of Patent: Oct. 4, 1988

[54] METHOD FOR REMOVING FAT AND FOR PURIFYING AND DEFOAMING LIQUIDS

[75] Inventor: William A. Thurman, El Toro, Calif.

[73] Assignee: Mederi Medical Systems, Inc., Tustin, Calif.

[21] Appl. No.: 738,452

[22] Filed: May 28, 1985

[51] Int. Cl.$^4$ ............... B01D 15/04; B01D 19/02
[52] U.S. Cl. ............................ 210/668; 210/692; 210/927; 55/87; 604/4; 604/5
[58] Field of Search ............... 210/289, 446, 927, 672, 210/679, 690–693, 668; 55/87; 604/4, 5

[56] References Cited

U.S. PATENT DOCUMENTS

| | | | |
|---|---|---|---|
| 4,017,279 | 4/1977 | Bowley | 210/927 X |
| 4,056,468 | 11/1977 | Breiter et al. | 210/672 |
| 4,202,775 | 3/1980 | Abe et al. | 210/927 X |
| 4,252,653 | 2/1981 | Beck et al. | 210/446 X |
| 4,476,023 | 10/1984 | Horikoshi et al. | 210/927 X |
| 4,568,367 | 2/1986 | Gremel et al. | 210/927 X |

Primary Examiner—Tom Wyse
Attorney, Agent, or Firm—Frank Frisenda; James A. Quinton

[57] ABSTRACT

A device and related method for use in defoaming and/or removing certain impurities from a fluid stream is disclosed. The device comprises a housing having an inlet and an outlet, and a filter media disposed between the inlet and outlet comprising a fat-absorbing, nonionic hydrophobic resin. A filter sock for retaining the filter media is disposed in the housing between the inlet and the outlet. The filter above described can be used to remove lipids and other materials from the fluid stream, or alternatively, can be treated with a fatty acid and used to defoam the fluid stream.

8 Claims, 2 Drawing Sheets

METHOD FOR REMOVING FAT AND FOR PURIFYING AND DEFOAMING LIQUIDS

BACKGROUND OF THE INVENTION

1. Field of the Invention

This invention relates to the field of fluid-treating devices and related methodologies, and more particularly to a device and realted method for removing lipids, and for purifying and defoaming fluids.

2. Prior Art

During the handling of blood, such as, for example, during open heart surgery, one distinct problem is that the blood has a tendency to foam. It is believed that this is caused by the blood trapping various gases in the form of small bubbles. In order to counteract and cause such blood bubbles to collapse, the prior art has evolved a number of filtration media which are treated with various defoaming agents. Examples of such devices are found in U.S. Pat. Nos. 3,507,395 and 3,898,054. One of the most popular defoaming agents is a silicon-based compound. While such compound is effective, at times traces of the silicon compound can be subsequently found in the blood, and its effect on the human body is not entirely understood. Further, many prior art devices which do act as good blood defoamers, are complex in their design. Thus, there is a need for a non-invasive, silicone-free, straight-forward means to prevent such bubbles from forming, or to cause such bubbles to collapse, and thereby defoam the blood.

Yet another problem associated with the treatment of blood has to do with the fact that blood often contains a high degree of cholesterol and other lipid materials. In order to deal with such high levels, various proposals have evolved, including dietary control and the like. The present invention is directed to a system pursuant to which blood is flowed through a filter media such that lipid materials in the blood stream are removed, thereby purifying the blood.

SUMMARY OF THE INVENTION

The present invention relates to a device which can be used alternatively to defoam a fluid, such as blood, or to remove certain lipid impurities from the fluid stream. In a first embodiment, the device comprises a housing having an inlet and an outlet, a solid particulate filter media disposed between the inlet and the outlet which includes a fat-absorbing nonionic hydrophobic resin. A filter sock is used to retain the solid particulate filter material between the inlet and the outlet. As fluid enters the device, it flows through the filter media where various lipid impurities are removed by the resin. A final filter may also be used to remove blood clots and the like as is well recognized in the art.

Alternatively, the resin can be treated with a fatty acid, and when so treated, it has been found that blood foam, when in contact with the treated resin, collapses, thereby releasing entrapped gas to the atmosphere.

The novel features which are believed to be characteristic of this invention, both as to its organization and method of operation, together with further objectives and advantages thereof will be better understood from the following description considered in connection with the accompanying drawing in which a presently preferred embodiment of the invention is illustrated by way of example. It is to be expressly understood, however, that the drawings are for the purpose of illustration and description only, and are not intended as a definition of the limits of the invention.

DETAILED DESCRIPTION OF THE INVENTION

Figure 1:
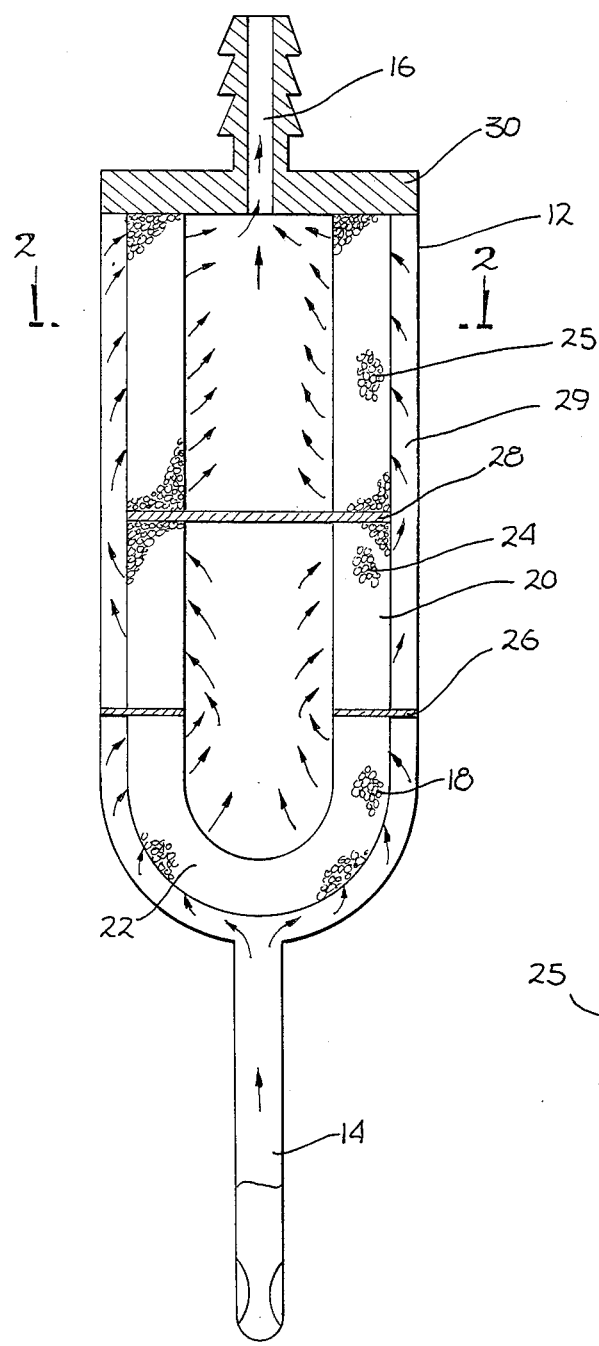
FIG. 1 is a sectional view showing the filter device of the present invention.

Referring first to FIG. 1, there is shown, as a presently preferred embodiment, the filter device 10 of the present invention. The device 10 includes a plastic housing 12 having an inlet 14 at one end thereof and an outlet 16 at the other end thereof. It should be understood that other configurations for the filter device are clearly within the scope of the present invention. Disposed between inlet 14 and outlet 16 is a specific particulate filter material which is a fat-absorbing, nonionic hydrophobic resin. Such resin is known in the art and is disclosed in U.S. Pat. No. 3,794,584, which is herein incorporated by reference. It is believed that such resin is sold under the trademark "Amberlite" by Rohm & Haas. As set forth in the '584 patent, one preferred resin which can be used in the device of the present invention is in the form of non-ionogenic macroreticular, cross-linked polymer beads. Such polymer beads can be made from a wide range of materials, such as polyethylenically unsaturated mononers. The polymer beads should have a porocity of at least 10%, perferably 40 to 95% and a specific surface area of at least 20 square meters per gram. It has been found that this particular resinous material has an affinity for lipid materials such as cholesterol, triglycerides and the like. While not to be bound by any theory, it is believed that the porocity and small particulate size (0.1 to about 3 mm.) of the resin beads causes the lipid material to adhere thereto and/or become trapped within the intersticial spaces of each of the beads.

Figure 2:
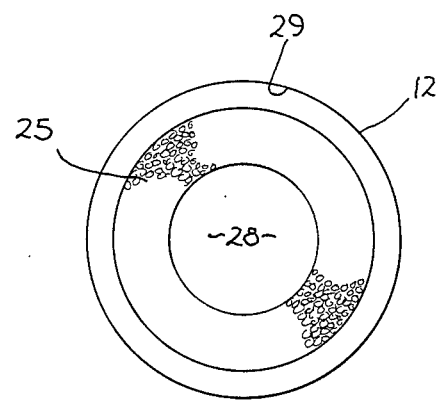
FIG. 2 is a section view taken along lines 2—2 and showing the filter media within the device.

Referring to FIGS. 1 and 2, such resin beads are illustrated as beads 18 which are retained by a nylon tricot filter 20. In order to insure complete removal of the lipid materials, the present invention contemplates the use of different resin bead "stages", wherein different resin beads are used in at least two of the stages. In the first embodiment, a first stage 22 is located adjacent the inlet 14, a second stage 24 is centrally located, and a third stage 25 is located adjacent the vacuum outlet 16. For example, the first stage could be an Amberlite resin known as XAD-4. This resin is a polymeric adsorbent in the form of white 20-30 mesh insoluble beads which is used to adsorb hydrophobic solutes. Such resin differs from ion exchange resins in that it has no ionic functional groups in its structure. Rather, it is a nonionic hydrophobic polymer which derives its adsorptive properties from its macroreticular structure, broad range of pore sizes and high surface area. Preferably, this resin has the following properties:

| | |
|---|---|
| Appearance | Hard, hydrated opaque beads |
| Average particle diameter | 0.35 to 0.45 mm |
| Harmonic mean particle size | 0.45 to 0.60 mm |
| True wet density | 1.03–1.04 gram/ml |
| Skeletal density | 1.080–1.09 gram/ml |
| Shipping weight | 44 lbs/ft$^3$ |

| | |
|---|---|
| Porosity of beads | 0.50 ml pore/ml of bead |
| Surface area | approximately 800 square meter/gram |
| Average pore diameter | 40-60 Angstrom units |

The second central stage 24 could be the same as first stage 22; alternatively it could be Amberlite XAD-2. This latter resin is similar to XAD-4, but has a somewhat lower porosity volume (51% vs. 42%) and surface area (750 m²/g vs. 330 m²/g;). However, the XAD-2 has a larger pore diameter than XAD-4 (50 Ang. vs. 90 Ang.).

The third stage 25 can also be XAD-2 or XAD-4. Yet another resin which is within the scope of this invention and which can be used in the first stage 22 is Amberlite 200. This resin is a macroreticular acidic cation exchange resin in the form of spherical beads. It has a density of 48 to 52 lbs./ft³ and a mesh size of 16 to 50. In its ionic form, this resin is sodium. The use of Amberlite 200 is to remove calcium from the blood, which therefore helps to prevent clotting.

As illustrated in FIG. 1, the first and second stages are separated by annular ring member 26. Ring member 26 is disposed in housing 12, such that all the fluid must first flow through the first stage 22 of the beads 18. A disk 28 is located in housing 12 such that the fluid is directed through second stage beads 24, along channel 29 and then through the third stage beads 25. Yet another annular ring 30 is placed in housing 12 such that fluid must pass through stage three beads 25 before flowing out the outlet 16.

In a first embodiment of the present invention, the device shown in FIGS. 1 and 2 is used, where there is no fatty acid initially disposed on the beads 18. Upon flowing blood through inlet 14, it contacts the beads 18, causing any lipid material in the blood to adhere thereto. The blood flowing through outlet 16 has been found to be substantially free of lipid materials. Unexpectedly, it has also been found that by trapping the fatty acids in the blood, foaming is substantially precluded.

In a second embodiment of the present invention, the beads are treated with a fatty acid such as oleic acid. Other fatty acid materials are also within the scope of the invention. In this embodiment, blood, such as from open heart surgery which is sucked up from a field of surgery, is directed through the filter 10. As mentioned above, of particular concern is the fact that blood foam may be formed which must be removed before the blood is returned to the patient. As the foamed blood comes into contact with the treated resin beads, the blood bubbles collapse. Again, while not to be bound by any theory, it is believed that the surface tension of the blood bubbles is weakened by the fatty acid so as to cause the blood bubbles to collapse, thus permitting substantially defoamed blood to be returned back to the cardiotomy reservoir or to a patient, or both. The use of the adding fatty acid materials brings even initial foaming to a substantially reduced level.

The filter illustrated in FIGS. 1 and 2 has been tested in an attempt to gain some information about lipid removal. Because there are a number of factors which affect removal of lipids from the blood (e.g., the percent lipid in the starting fluid, flow rate, etc.), the results should be viewed in that light. Using XAD-4 as the resin beads, and making multiple passes through the filter shown in FIGS. 1 and 2, total lipid content of normal bovine blood was reduced about 24 percent at a flow rate of 3.0 to 3.5 liters per minute for 30 minutes. For the same flow rate, cholesterol removal was from about 30%. These are perceived to be very good results, and other configurations for the filter will likely reduce lipid and cholesterol levels even further. For example, if lower flow rates are used, and/or more passes are made through the filter, even better results are obtained. Lipid removal as high as 41% for one pass, cholesterol removal of 48% and triglycerides of 69% have been obtained.

Although this invention has been disclosed and described with reference to particular embodiments, the principles involved are susceptible to other application which will be apparent to persons skilled in the art. For example, the resin beads can be embedded in a filter material or can be used in a wide variety of different configuration of filters.

Figures 3, 4:
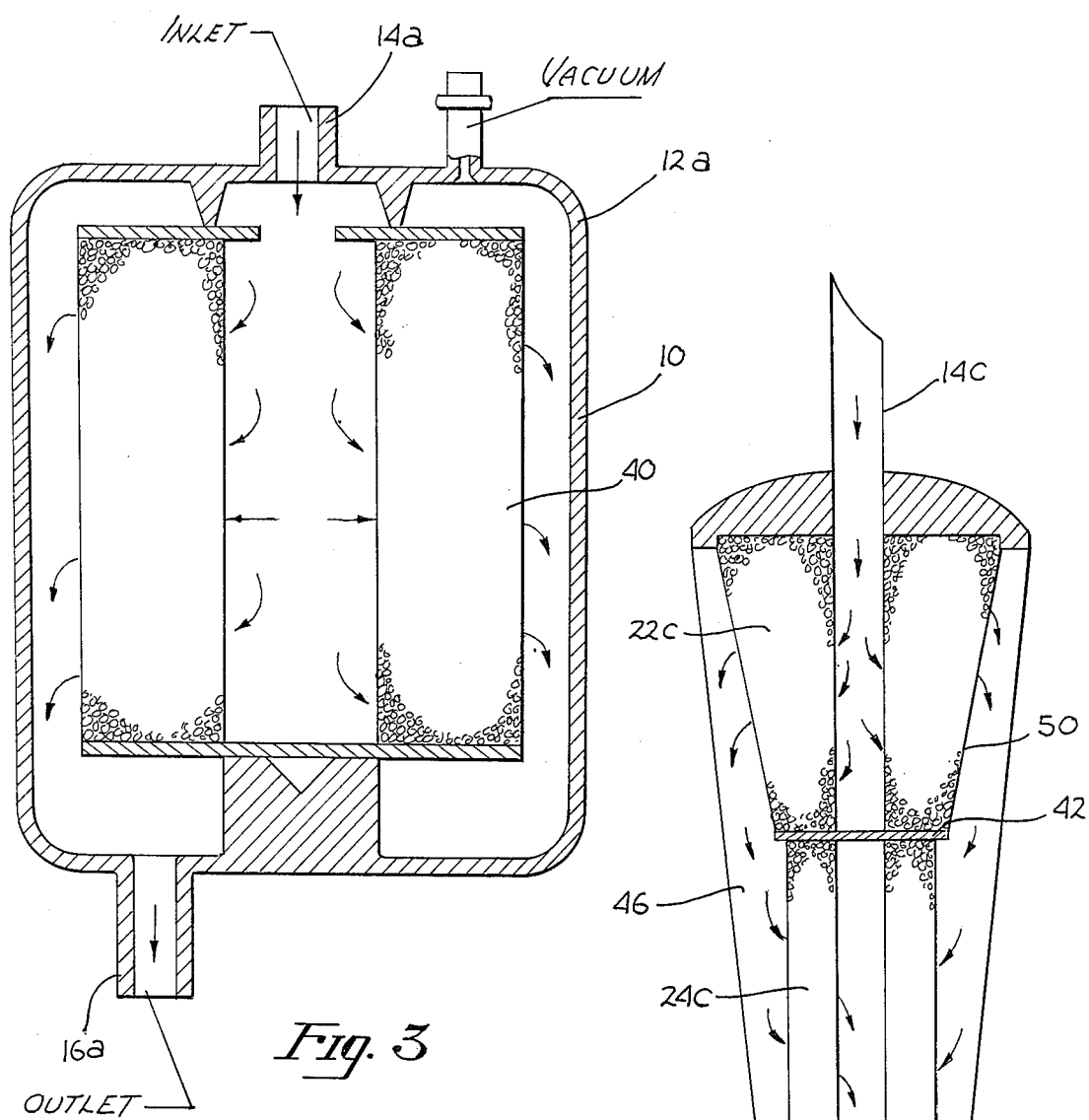
FIGS. 3 and 4 show other embodiments of the filter device of the present invention.

In FIG. 3, the housing 12a has an inlet 14a at one end thereof and an outlet 16a at the other end thereof. An annular filter 40 is disposed there between. Such filter 40 can include XAD-2, XAD-4 or mixtures thereof. Such configuration, while helpful in the removal of fat from blood, is not believed to be as effective as that shown in FIGS. 1 and 2. However, the configuration illustrated in FIG. 3 is straightforward in its construction, easy to assemble and is believed to have desirable pressure built-up characteristics.

FIG. 4 shows yet another embodiment for the device of the present invention. In the embodiment shown in FIG. 4, blood flows in through inlet 14c, passes through filter 50 and out through outlet 16c. Disk 42 divides the filter into first and second stages, and because of the location of inlet 14c, all of the blood must pass through the first upper stage 22c. The location of annular ring 44 adjacent outlet 44 helps insure that contact of the blood with the second stage 24c is achieved. As one can see, as the blood passes through first stage 22c, it flows along channel 46. However, flow out of the bottom of the dune is precluded by annular ring 44 unless the blood first flows through the second stage 24c. Other configurations for the filter are thus within the scope of the invention. Further, fluids other than blood can be passed through the filter for defoaming or lipid removal purposes. This invention, therefore, is not intended to be limited to the particular embodiments herein disclosed.

What is claimed is:

1. A method for removing lipids from a fluid comprising the steps of:
   (a) providing a bed of a fat adsorbing, nonionic hydrophobic resin beads; and
   (b) removing lipids from said fluid by flowing a lipid-containing fluid through said bed whereby said lipids adhere to said resin beads.

2. The method according to claim 1 wherein said fluid is blood, and said resin beads are made of a cross-linked polystyrene.

3. A method for defoaming a fluid comprising the steps of:
   (a) providing a bed of a fat-adsorbing, nonionic, hydrophobic resin beads, said beads being treated with a fatty acid; and
   (b) defoaming said fluid by flowing said fluid through said bed such that foam in said fluid collapses and entrapped gases are released.

4. The method according to claim 3 wherein said fluid is blood.

5. The method according to claim 4 wherein said fatty acid is metabolizable in the human body.

6. The method according to claim 5 wherein said fatty acid is oleic acid.

7. A method for providing defoamed blood for use during surgery comprising,
(a) recovering blood lost by a patient during surgery;
(b) defoaming said blood by;
  (i) providing a bed of a fat-adsorbing nonionic, hydrophobic resin beads; said beads having an average pore diameter of from about 40 Å to about 90 Å;
  (ii) flowing said blood through said bed such that foam in said blood collapses and entrapped gasses are released;
(c) returning said defoamed blood to the patient.

8. The method according to claim 7 wherein said resin beads are treated with a fatty acid.

* * * * *